United States Patent [19]

Castner, Sr. et al.

[11] 4,236,637
[45] Dec. 2, 1980

[54] COTTON SWAB VENDER

[75] Inventors: J. Fred Castner, Sr., P.O. Box 7156, San Diego, Calif. 92107; John F. Castner, Jr., Torrance, Calif.

[73] Assignee: J. Fred Castner, Sr., San Diego, Calif.

[21] Appl. No.: 49,631

[22] Filed: Jun. 18, 1979

[51] Int. Cl.³ .................... B65D 83/02; B65D 85/20
[52] U.S. Cl. .................................. 206/467; 206/470; 206/362
[58] Field of Search ............... 206/362, 461, 467, 470, 206/45, 34, 44, 12, 361

[56] References Cited

U.S. PATENT DOCUMENTS

| 2,847,119 | 8/1958 | La Padura | 206/362 |
| 3,371,848 | 3/1968 | Ward et al. | 206/621 |
| 3,398,877 | 8/1968 | Jacobson | 206/621 |
| 3,746,155 | 7/1973 | Seeley | 206/470 |

Primary Examiner—William T. Dixson, Jr.
Attorney, Agent, or Firm—Hill, Van Santen, Steadman, Chiara & Simpson

[57] ABSTRACT

A package for marketing and vending strips of cotton swabs has one or more molded plastics material tray-like blisters with swab carrying strips stacked therein holding the swabs in spaced protected position. The blister is sealed to and covered by a cardboard backing which has a flap providing a flat bottom wall and openable to a dispensing outlet. The preferred flap has a fold line above the bottom edge of the backing providing a door portion connected to the backing along its sides by tear lines, a tab portion depending from the door portion foldable under the blister to provide a flat bottom wall for the package and a tongue portion foldable over the front bottom end of the blister with an end releasably tucked into pockets or grooves in the blister. When the tongue is released, the flap can be pulled backward to sever the tear lines and open the door portion giving access to the interior of the blister exposing the strips for dispensing the swabs. An opened package is closed by pulling the flap forwardly and tucking the tongue into the grooves. The bottom of the blister has a raised central portion supporting the stack of strips and a thumb receiving recess in this raised portion facilitates pulling the strips through the doorway to dispense the swabs. The cover or backing has a hook receiving hole in the top thereof to suspend the package for display or vending.

18 Claims, 12 Drawing Figures

U.S. Patent Dec. 2, 1980 Sheet 1 of 2 4,236,637
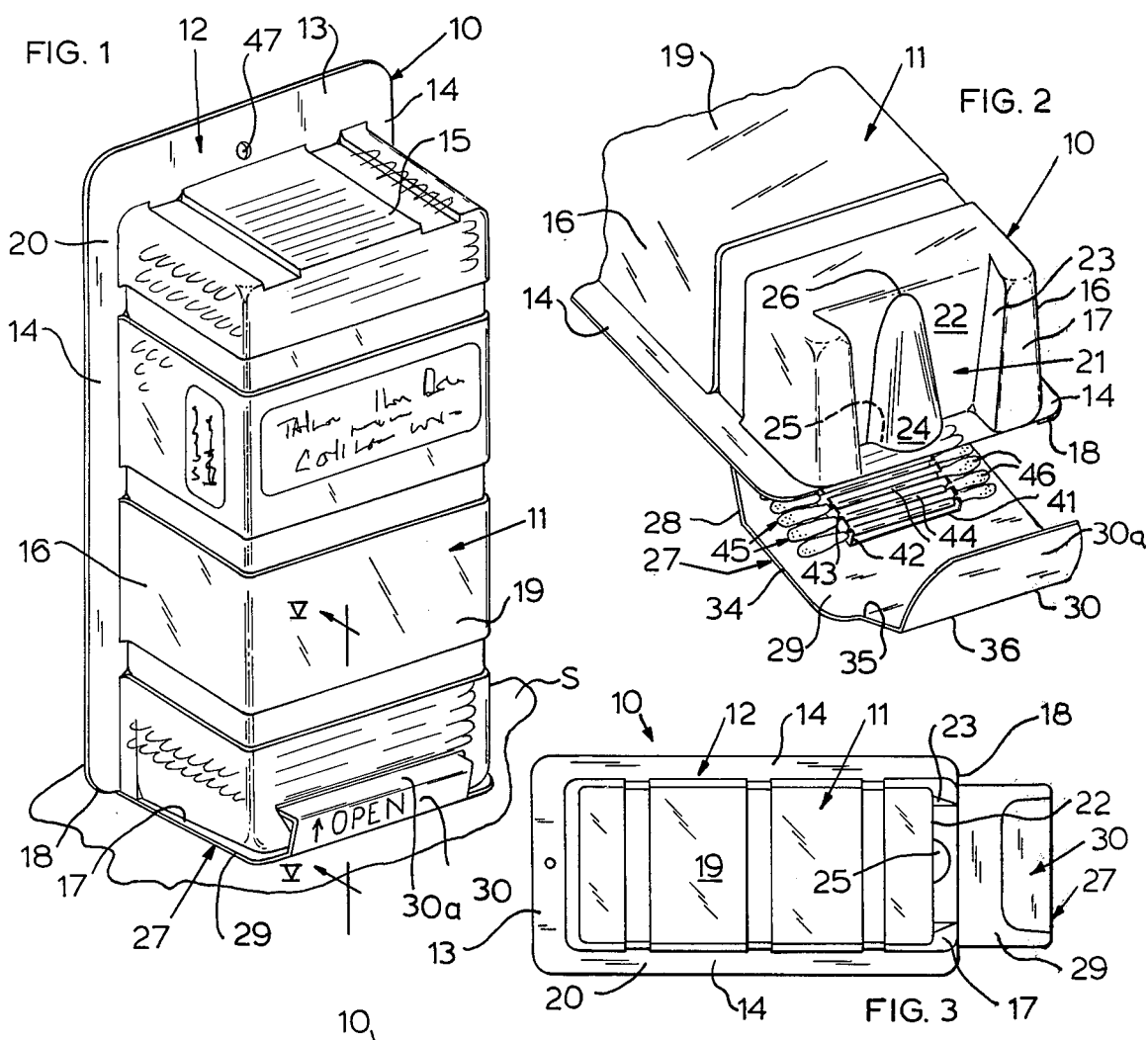
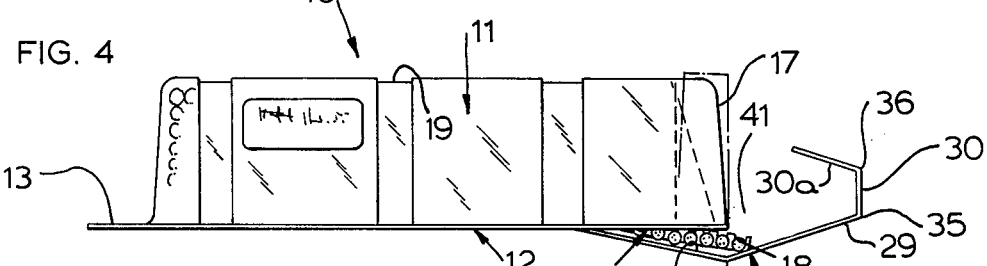
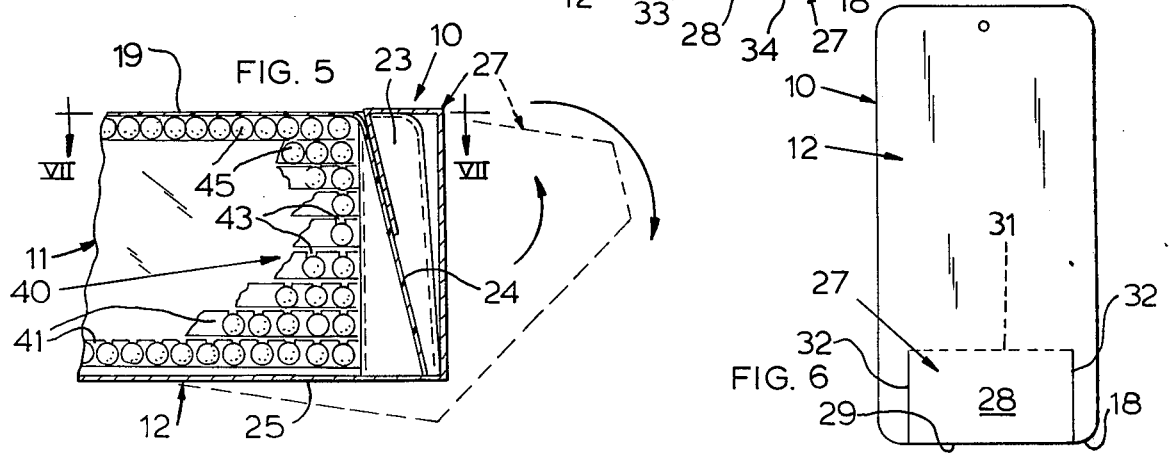

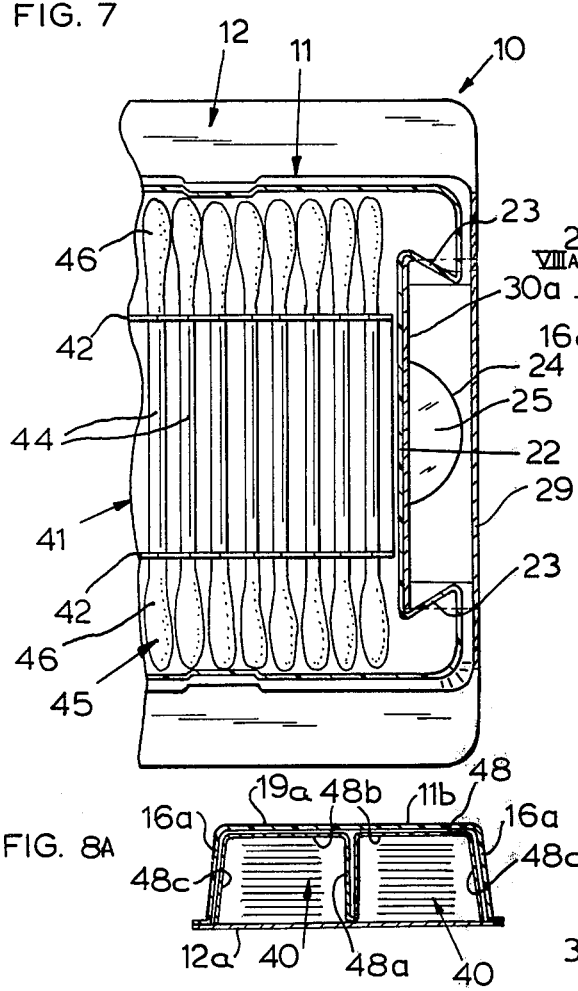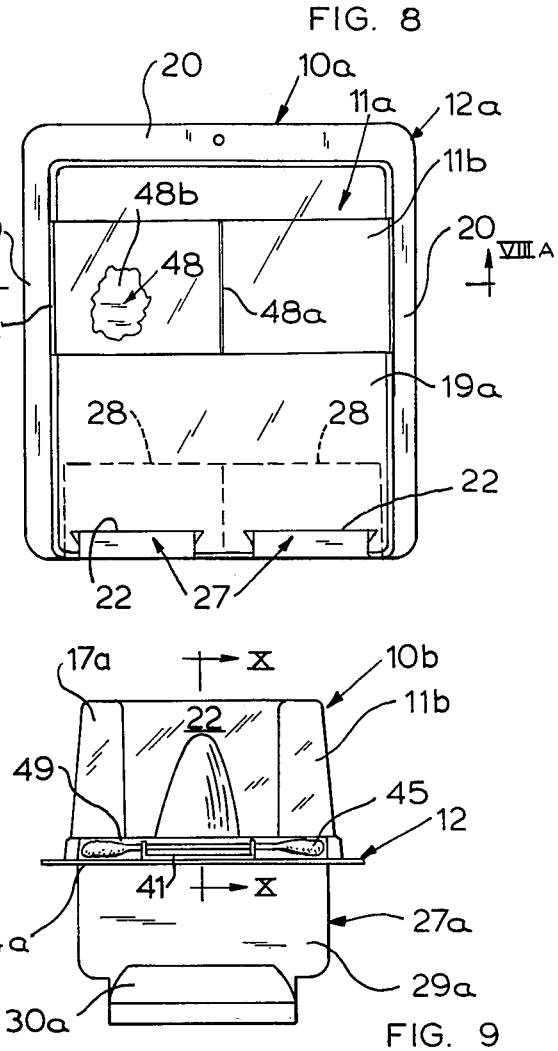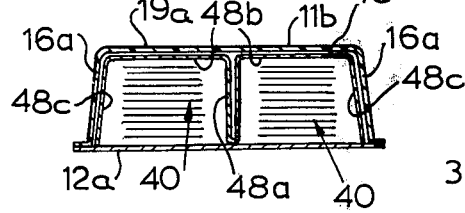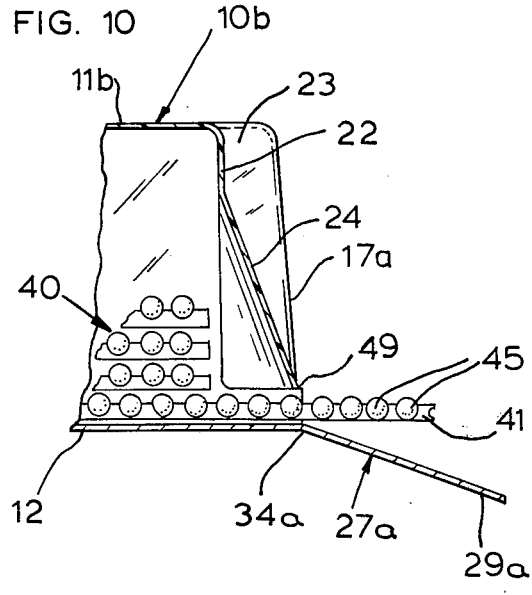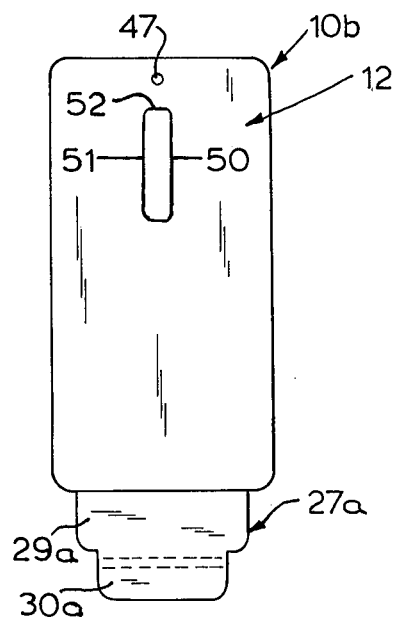

COTTON SWAB VENDER

FIELD OF THE INVENTION

This invention deals with dispensing packages for strip carried products and specifically relates to a cardboard backed blister package with an easily manipulated flap that opens and closes a strip dispensing outlet at the bottom of the cardboard backing.

Prior Art

Heretofore dispensers for cotton swabs carried on strips were separate from packages in which the swabs were marketed, had to be loaded with the strips, and required mechanical dispensing linkages or were in the form of boxes or cylinders from which a single wound roll of tape could be pulled to dispense products carried on the tape. It would therefore be an improvement in the art to provide an inexpensive blister type resealable package for marketing and dispensing strip mounted cotton swab applicators and the like products.

SUMMARY OF THE INVENTION

According to this invention a cardboard backed tray-like blister package has a flap on the backing covering a dispensing opening and forming a bottom for the package. The preferred flap is connected to the backing by a transverse fold line above the bottom end of the backing with tear lines along the sides thereof that are easily severed to open the interior of the blister along an area of the bottom thereof forming a doorway through which the contents of the blister can be dispensed. The flap includes a portion foldable under the bottom of the blister and over the front bottom end of the blister to be tucked into pockets or grooves formed in a raised portion of the bottom of the blister. This raised portion provides a bottom wall which supports the products in the package and which preferably has a recess providing a thumb hole to grasp a product to be dispensed. The package is easily opened by pulling the tongue out of the grooves and swinging the flap backward to open the doorway. This doorway is completely within the confines of the cardboard backing and puncturing of the blister to give access to the contents is not required. An open package is easily closed by pulling the flap forwardly to seat in the doorway, extend under the blister, and tucked back into the grooves.

In a preferred arrangement cotton tipped swabs are carried in spaced relation transversely across a cardboard mounting strip with their stick portions engaged in notches along the sides of the strip. A stack of such strips fits freely in the tray-like blister which is preferably molded from transparent polyolefin plastics sheet material, such as polyethylene or polypropylene, in the form of a cup or tray with an outturned peripheral flange sealed to the cardboard backing or cover except at the flap portion of the backing. The molded cup or tray is relatively stiff to prevent crushing of the contents but is sufficiently flexible to accommodate some deformation without fracture or cracking.

A preferred shape for the molded tray portion of the blister is rectangular with a tray depth sufficient to accommodate about 8 to 10 layers of swab carrying strips being very practical. The swabs are thus separated from each other and are protected against damage such as can occur when loose swabs are piled in a tray. The bottom of the preferred tray has a raised central portion with tapered sidewalls providing the grooves into which the tongue of the flap is tucked. The stack of strips rests on this raised bottom wall and its central portion preferably has a recess providing a thumb hole to grasp the leading end of the strips for pulling the swabs through the dispensing outlet when a flap is opened. Each individual swab can thus be dispensed without touching or polluting another swab.

It is then an object of this invention to provide a marketing and vending package for swab applicators carried on strips that are stacked in the package and selectively pulled through a dispensing outlet that is opened and closed by a flap.

Another object of the invention is to provide a cotton swab vender which houses a stack of cardboard strips carrying the swabs in side by side relation and selectively pulled through a dispensing outlet closed by a flap forming a bottom for the package.

A specific object of the invention is to provide a blister type dispensing package for strips of cotton swabs which has a cardboard backing providing with a flap foldable under the bottom of the blister and releasably tucked in the front face thereof to be pulled therefrom to open the dispensing outlet.

Another object of the invention is to provide a tray type dispensing package with a cardboard cover having a flap releasably tucked in the bottom of the tray and adapted to be pulled to open a doorway giving access to the tray.

A specific object of the invention is to provide a package having a molded plastics material rectangular tray with an outturned periphery sealed to a cardboard backing or cover and an open bottom end closed by a cover flap which forms a bottom wall for the package.

Another object of this invention is to provide a multiple tray package for selectively dispensing strip carried products through outlets that are closed by bottom flaps on a single cover or backing sealed to the peripheries of the trays.

Another object of the invention is to provide a package which seals a stack of strip carried sticks such as cotton swabs or toothpicks, and has a bottom flap releasably tucked therein and adapted to be swung to an open position for dispensing the products.

Other and further objects of the invention will become apparent to those skilled in this art from the following detailed description of the annexed sheets of drawings which, by way of preferred examples show several embodiments of the invention.

ON THE DRAWINGS

FIG. 1 is a front and side perspective view of a vending package of this invention in an upright closed position.

FIG. 2 is a perspective view of the bottom portion of the package of FIG. 1 in an opened position.

FIG. 3 is a top plan view of the package of FIG. 1 but in the opened position of FIG. 2.

FIG. 4 is a side elevational view of the package of FIG. 1 showing the closed position in dotted lines and the opened position in solid lines.

FIG. 5 is a fragmentary longitudinal cross sectional view along the line V—V of FIG. 1 and illustrating an opened position in dotted lines.

FIG. 6 is a back elevational view of the package of FIG. 1.

FIG. 7 is a fragmentary cross sectional view along the lines VII—VII of FIG. 5.

FIG. 8 is a front elevational view of a twin package according to this invention.

FIG. 8A is a cross sectional view, on a smaller scale, along the line XIIIA—XIIIA of FIG. 8.

FIG. 9 is a bottom end elevational view of a modified dispensing outlet for the packages of this invention.

FIG. 10 is a fragmentary cross sectional view along the line X—X of FIG. 9.

FIG. 11 is a back elevational view of the package of FIGS. 9 and 10.

AS SHOWN ON THE DRAWINGS

The reference numeral 10 of FIGS. 1 through 7 illustrates a first embodiment of the vending package of this invention. The package 10 has a tray-like molded plastics sheet blister 11, preferably embossed with stiffening ribs as shown, and covered by a cardboard backing 12 which has a wide top margin 13 and narrower side margins 14 projecting beyond the top end 15 and the sidewalls 16 of the tray 11. The bottom wall 17 of the tray is flush with the bottom edge 18 of the backing 12. The front face 19 of the tray 11 is flat.

An outturned peripheral flange 20 extending along the top 15 and sides 16 of the tray 11 is bonded to the top margin 13 and side margins 14 of the cardboard backing 13 so that the open face of the tray 11 is completely covered by and sealed to the backing 12.

The bottom 17 of the tray has a raised central portion 21 with a flat top wall 22 and tapered sidewalls 23 converging toward each other from this top wall 12 to the bottom 17 and providing grooves or pockets along the lengths thereof. The central portion of the raised flat top 22 is fluted or depressed at 24 forming a semi-cylindrical recess or thumb hole 25 which opens to the open face of the tray. The shape of the depression 24 is preferably tapered from a full semi-circular open end portion to a closed shallow nose 26 (FIG. 2) terminating within the confines of the raised portion 22.

The cardboard backing or cover 12 has a flap 27 at the bottom end thereof with a door portion 28, a bottom portion 29 and a tongue portion 30. The door portion 28 as illustrated in FIG. 6 is cut from the bottom end of the backing 12 and is connected thereto by a transverse fold line 31 and longitudinal perforated tear lines 32. The fold line 31 is spaced above the bottom edge 18 of the backing 12 for a sufficient distance to provide a doorway or dispensing opening 33 to the interior of the tray 11 when the flap is pulled back from the cover to give ample access to the contents of the tray. This door portion 28 of the flap 27 terminates flush with the bottom edge 18 of the backing 12 but is connected through a fold line 34 with the bottom portion 29 of the flap which covers the bottom 17 of the blister. The flap portion 29 is sufficiently wide to completely overlie the recessed portion 21 of the blister bottom 17 and to rest on the bottom.

The tongue portion 30 of the flap 27 is somewhat narrower than the bottom 29 and is connected thereto by a fold line 35. The tongue 30 extends over the bottom front face of the tray or blister 11 and has a rounded tip end 30a that is tucked into the grooves or pockets 23 thereby holding the flap in a closed position covering the doorway 33 and the bottom 17 of the blister. However when the tip end 30a of the tongue is extracted from the pockets or grooves 23 and the flap is pulled backward to an open position, the doorway 33 will be exposed and the contents of the tray are accessible for dispensing. In the closed position of the flap, on the other hand, the contents of the tray are sealed.

According to this invention the tray is filled with a stack 40 of cardboard strips 41 having upturned side margins or flanges 42 along the lengths thereof with notches 43 receiving the sticks 44 of cotton swabs 45 releasably therein to carry the swab in spaced side by side relation across the strip. The turned up margins or flanges 42 engage each stick 44 just inwardly from the cotton tips 46 of the swab. Each cotton tip 46 thus lies outwardly from the strip and is held in spaced relation from the strips and adjacent swabs to prevent crushing. The swabs are thus held against piling up in the package and are always available at the dispensing outlet.

The tray 11 has a width dimension to freely receive the cotton swabs with the cotton tips avoiding a wedge fit with the sidewalls of the tray. The length of the tray is sufficient to freely receive the strips lengthwise. The strips are sufficiently long so that each strip can carry about three dozen swabs. The depth of the tray is sufficient to freely house a stack of about 8 to 10 swab carrying strips.

The package 10 in its closed flap condition has a flat bottom provided by the botton portion 29 of the flap so that the package can rest in an upright or vertical position from a support surface S of a sink, table, or the like. From this position the package can be laid flat as shown in FIG. 4 with the flap 27 pulled to an open position and swabs from the bottom strip 41 of the layer 40 can be pulled through the open doorway 33 to be dispensed.

In addition, the package 10 can be suspended from a hook or peg on a vertical surface and for this purpose a hole 47 is provided through the top margin 13 of the backing or cover 12 to receive the hook or peg. Then with the flap 27 spaced above a support surface S, the flap can be pulled to the open position for dispensing the swabs from the bottom of the package.

In the modified package 10a of this invention, as shown in FIGS. 8 and 8A a double width tray-like blister 11a is mounted on and sealed to a wide backing or cover 12a, being sealed to the backing along the marginal flanges 20 thereof in the same manner as described in FIGS. 1 through 7. The wide blister 11a has two raised bottoms 22 receiving the same flaps 27 as the blister 11 of FIGS. 1 to 7 and the wide backing 12a has a door portion 28 of each flap opening an access door to each raised bottom of the wide blister 11a exactly as in the package 10. Two stacks 40 of swab carrying strips 44 are positioned in side by side relation in the wide blister 11a to be dispensed through the side by side doors 28.

A cardboard band 48, folded in the form of an "M" fits in a recess provided by a stiffening rib embossment 11b in the front face 19a and sidewalls 16a of the blister 11a. The band is folded to provide a central dividing leg 48a which forms a separator between the side by side stacks 40 of swabs, and has top walls 48b overlying the stacks 40 and end legs 48c underlying the embossed sidewalls 16a and overlying the outer side edges of the stacks 40. The legs 48a and 48c of the band 48 may rest on the backing 12a to seat the top walls 48b in the recess provided by the embossment 11b so that the band 48 will remain over and between a central portion of the side by side stacks 40. If desired the folded portion forming the dividing leg 48a may have the opposed walls thereof secured together.

Alternately, if desired, a straight flat cardboard strip could be inserted between the side by side stacks in place of the cardboard band 48. However this band 48 provides top and end walls which can be printed with identifying or advertising indicia.

It will therefore be understood that the modified package 10a of FIGS. 8 and 8A provides a plurality of dispensers on a single mounting.

Also, alternately, a plurality of dispensers on a single mounting can be provided by a pair of single width blisters 11 such as shown in FIGS. 1 through 7 mounted in side by side relation on a single backing such as 12a of FIGS. 8 and 8A thus providing a twin package dispenser.

In the embodiment of 10b of FIGS. 9–11, the same backing or cover 12 of the embodiment 10 covers and seals a slightly modified tray-like blister 11b in the same manner as in the embodiment of FIGS. 1 to 7 but the backing 12 has a modified flap 27a which does not have the door portion 28 of the flap 27 but instead is connected to the bottom edge of the backing 12 by a fold line 34a to provide a bottom cover portion 29a and to be swung from a closed position with its tongue 30a tucked in the grooves of the blister to an open position shown in FIG. 10. In this open position, a slot 49 cut in the bottom end 17a of the blister 11b is exposed to give access to the bottom strip 41 of swabs 45 in the stack 40 housed in the blister 11b.

To facilitate pulling of the bottom strip 41 through the dispensing slot 49, as shown in FIG. 11, the cardboard backing or cover 12 can have a tear out section 50 connected along a tear line periphery 51 to be pulled out to expose the bottom strip 41 permitting it to be pushed through the slot 49 to dispense the swabs 45. If desired this tear out section 50 can be permanently connected to the backing 12 along a fold line 52 so that it may be pushed back into closed position after a strip has been ejected through the slot 49.

From the above descriptions it will therefore be understood that this invention provides an inexpensive, lightweight, dispensing or vending package for strip carried products such as cotton swabs. The package displays its contents, can be suspended from a hook or pin or rest on a support surface either in an upright or flat position and has a flap which is easily tucked into closed position or pulled to an open position giving access to a dispensing outlet. It is also to be understood that numerous departures from the specific disclosures of the preferred embodiments of this invention as shown in the drawings, may be made without avoiding the scope of this invention as defined in the claims hereof.

We claim as our invention:

1. A package for marketing and vending products carried on strips stacked in the package which comprise a tray-like blister with a front face, a top end, a bottom wall and side walls for housing the strips, a backing covering and sealed to said blister extending above the top end of the blister and having an aperture therein adapted to receive a hook to hang the package from a wall, said package having a dispensing outlet at the bottom wall of the blister, and a flap on said backing folded over said outlet and across the bottom wall of the blister, a tongue portion on said flap foldable over the front face of the blister, tongue retaining grooves in the blister having openings into the front face of the blister and said flap forming a flat bottom wall under the bottom wall of the blister supporting said package in an upright position when said tongue is tucked into said groove openings whereby said flap is held in a closed position over said outlet by tucking the tongue thereof into said groove openings and is pulled to an open position exposing the dispensing outlet.

2. The package of claim 1 wherein the blister has a raised central bottom end portion and the tongue retaining grooves are provided by converging sidewalls between the raised central portion and the bottom of the blister.

3. The package of claim 1 wherein the dispensing outlet is a doorway in the backing closed by a portion of said flap.

4. The package of claim 1 wherein the dispensing outlet is a slot in an end of the blister closed by the portion of the flap extending across the end of the blister.

5. The package of claim 1 wherein the flap has a portion providing an end wall flush with the bottom end of the backing to support the package in an upright position.

6. The package of claim 1 wherein the blister and the backing are sufficiently wide to house two stacks of strips in side by side relation, a dispensing outlet is provided for each stack and a flap is provided for folding over each outlet.

7. The package of claim 6 including a separator between the two stacks of strips in the package.

8. The package of claim 6 including a cardboard band folded in the shape of an "M" embracing each stack of strips and providing a divider between the stacks.

9. The package of claim 8 wherein the blister has a raised embossment providing a recess receiving the "M" shaped band.

10. The package of claim 1 wherein the flap has a door portion swingable on a transverse fold line on the backing and connected along its sides by perforated tear lines and wherein a bottom portion of the flap is connected to the door portion by a fold line and wherein the tongue portion of the flap is connected to the bottom portion by a fold line.

11. A package for marketing and vending strips of cotton swabs which comprises a molded sheet plastics material tray blister having a front face and peripheral walls sized to house a stack of swab carrying strips, a backing covering said tray blister and sealed to said peripheral walls, a bottom flap on said backing covering a peripheral wall of said tray blister forming a flat bottom wall supporting the package in an upright position and cooperating with said tray blister to open and close access to strips in the tray, said tray having a recess in the front face thereof, and said flap having a free end releasably received in said recess to hold the flap in closed flat position.

12. The package of claim 11 wherein the bottom flap is foldable over an end of the blister to form a bottom wall thereof and is then folded over a front face of the blister into the recess.

13. The package of claim 11 wherein access to the strips in the tray is provided by a portion of the flap cut from the backing and connected thereto by a transverse fold line.

14. The package of claim 11 wherein access to the strips in the tray is provided by an end slot in the blister.

15. The package of claim 11 wherein the flap is folded under the blister and over a front face of the blister into the recess.

16. A blister package for vending products stacked therein through a dispensing outlet in an end thereof which comprises a backing sheet, a plastics blister sealed on the sheet and cooperating therewith to provide a dispensing outlet for the contents thereof, a flap on said backing sheet foldable over the blister forming a flat bottom for the package supporting the package in an upright position and having a tongue releasably tucked into the blister to close the dispensing outlet, and said flap being swingable on the backing to open the dispensing outlet.

17. The package of claim 16 wherein the blister has a raised central bottom portion with converging sidewalls providing recesses into which the tongue of the flap is tucked.

18. The package of claim 16 wherein the flap provides a bottom wall and the backing has a top margin portion with a hole therethrough to receive a fastener for suspending the package.

* * * * *